United States Patent [19]
Zhong et al.

[11] Patent Number: 5,874,101
[45] Date of Patent: Feb. 23, 1999

[54] BIOACTIVE-GEL COMPOSITIONS AND METHODS

[75] Inventors: Jipin Zhong; David C. Greenspan, both of Gainesville, Fla.

[73] Assignee: USBiomaterials Corp., Alachua, Fla.

[21] Appl. No.: 834,155

[22] Filed: Apr. 14, 1997

[51] Int. Cl.$^6$ ........................................... A61F 2/28
[52] U.S. Cl. ..................... 424/426; 523/114; 523/115; 523/116
[58] Field of Search .................................. 523/114, 115, 523/116; 424/426

[56] References Cited

U.S. PATENT DOCUMENTS

| | | |
|---|---|---|
| 4,849,378 | 7/1989 | Hench et al. . |
| 4,851,150 | 7/1989 | Hench et al. . |
| 4,851,373 | 7/1989 | Hench et al. . |
| 5,071,674 | 12/1991 | Nogues et al. . |
| 5,074,916 | 12/1991 | Hench et al. . |
| 5,076,590 | 12/1991 | Steinetz et al. . |
| 5,076,980 | 12/1991 | Nogues et al. . |
| 5,147,829 | 9/1992 | Hench et al. . |
| 5,196,382 | 3/1993 | Hench et al. . |
| 5,222,092 | 6/1993 | Hench et al. . |

OTHER PUBLICATIONS

Brinker, C. Jeffrey and Scherer W. Scherer. "Drying." *Sol–Gel Science, the Pyysics and Chemistry of sol–Gel Processing.* pp. 500–503.

Brinker, C. Jeffrey and Schemer W. Schemer. "Hydrolysis and Condensation." *Sol–Gel Science, The Physics and Chemistry of Sol–Gel Processing,* pp. 116–119.

Hoellrich, R. G., Chamberland, D. L., Stokes, K. E., McLoughling, S. W., and Wheeler, D.L. "In Vivo Evaluation of sol–Gel Bioglass." (Part II: Mechanical Compression Strength at 4 Weeks).

Pereira, Marivalda M., and Clark, Authur E., and Hench, Larry L. "Effect of Texture on the Rate of Hydroxyapatite Formation on Gel–Silica Surface," *J. Am. Ceram. Soc.,* v78(9): pp. 2463–2468(1995).

Thomas, Ian M. "Multicomponent Glasses from the Sol–Gel Process," *Sol–Gel Technology for Thins Films, Fibers, Preforms, electronics, and specialty Shapes.* pp. 1–15. (Rutgers –The State University of New Jersey). edited by Lisa C. Klein.

Wheeler, D. L. and Stokes, K. E. "In View Evaluation of Sol–Gel Bioglass." (Part I: Histological Findings).

*Primary Examiner*—Carlos A. Azpuru
*Attorney, Agent, or Firm*—Burns, Doane, Swecker & Mathis, L.L.P.

[57] ABSTRACT

A process for making bioactive glasses is described including preparing a reaction mixture of reactants capable of forming a sol-gel, aging the reaction mixture, near equilibrium drying a gel resulting from the reaction mixture, and heating the -near equilibrium-dried gel described. Also described are near equilibrium-dried bioactive glass compositions.

27 Claims, 13 Drawing Sheets

BIOACTIVE-GEL COMPOSITIONS AND METHODS

FIELD OF THE INVENTION

The present invention relates to bioactive glass compositions, for example, used for filling bone defects, and bioactive compositions produced by a sol-gel process. The present invention also relates to various methods for making sol-gel bioactive glasses and methods of treatment using bioactive glasses.

BACKGROUND OF THE INVENTION

Sol-gel processes for making bioactive glass using sol-gel technology are generally known. For example, U.S. Pat. No. 5,074,916 (the "'916 patent"), the subject matter of which is incorporated herein by reference, discloses sol-gel processing techniques used to produce alkali-free bioactive glass compositions based on $SiO_2$, CaO and $P_2O_5$. The '916 patent discloses that by varying the $SiO_2$ content, a range of hydroxyapatite production rates can be obtained. Also, varying the time of exposure to actual or simulated in vivo solutions permits use of a range of allowable proportions of $SiO_2$. The sol-gel derived compositions disclosed in the '916 patent can be chosen to achieve target values for a thermal expansion coefficient, elastic modulus and volume electrical resistivity.

The processes and compositions described in U.S. Pat. No. 5,074,916 have certain disadvantages. For example, the process of the '916 patent does not provide for bioactive glasses having large pore sizes. This results in a relatively low rate of hydroxycarbonate apatite ("HCA") development when the glasses are exposed to biological fluids and tissues. See "Effect of Texture on the Rate of Hydroxyapatite Formation on Gel-Silica Interface", J. Am. Ceram. Soc., 78[9] 2463–68 (1995), the subject matter of which is herein incorporated by reference. Moreover, the resultant product lacks homogeneity, stability and can only be heated to a limited extent during preparation. Also, the resultant product lacks an acceptable level of resorbability.

Other examples of sol-gel processes can be found in Thomas, "Multicomponent Glasses From the Sol-Gel Process", Noyes Publications edited by Lisa C. Klein of the Center for Ceramics Research, College of Engineering, Rutgers, Piscataway, N.J. and "Sol-Gel Science—The Physics and Chemistry of Sol-Gel processing", Brinker et al., Academic Press Inc. These publication are also incorporated by reference.

Previous methods for preparing monoliths of bioactive glasses have also proven unsatisfactory. Earlier methods required the use of various toxic chemicals in an effort to avoid cracking of the monolith during drying. U.S. Pat. No. 4,849,378 ("the 378 patent"), incorporated herein by reference discloses a method of fabricating an ultraporous silicon dioxide containing gel monolith having a predetermined mean pore size by controlling temperature, duration and other conditions of aging. The '378 patent discloses that the use of a drying control chemical additive is important and formamide is the additive of choice. Similarly, U.S. Pat. No. 4,851,150 ("the '150 patent") addresses drying control chemical additives for rapid production of large sol-gel derived monoliths. The '150 patent also discloses drying in a methanolic atmosphere. Both of these methods are unsatisfactory because they require the use of chemical additives.

Other early work in U.S. Pat. No. 5,076,980 (incorporated by reference) used drying under humidity environment and sintering under some gas atmosphere to make a sol-gel monolith. However, the focus of such procedures was the fabrication of crack-free and fully dense silica glass and the pore texture of the monolith was not mentioned. Moreover, this patent does not address the preparation of a bioactive glass.

Accordingly, it is an object of the present invention to provide a sol-gel process, particle and monolith that yield bioactive glasses used for bone grafting and filling osseous defects, having larger pore size at a given level of silicon dioxide in the final composition, faster HCA formation, better resorbability, and better homogeneity. It is further an object of the present invention to provide for precise control of rates of resorbtion.

SUMMARY OF THE INVENTION

The present invention is directed to a process for making bioactive glasses used, for example, for bone grafting including; preparing a reaction mixture (sol) capable of forming a gel, aging the reaction mixture, near equilibrium drying a gel resulting from the reaction mixture, and heating the near equilibrium-dried gel. The present invention is also directed to dried bioactive glass compositions and monolithic bioactive compositions having improved resorbability. The present invention is further directed to materials suitable for bone grafting, repairing of tissue defects and other orthopedic uses.

BRIEF DESCRIPTION OF THE DRAWINGS

FIG. 4 58S sol-gel glass produced by near-equilibrium drying at 4 weeks post-op. Rapid bone formation is noted even in the center of the defect (solid arrows). Resorption of many particles can already be seen (open arrows).

FIG. 5 58S sol-gel glass at 8 weeks. Extensive bond formation is noted throughout the defect. Most of the particles have already resorbed, and are replaced by newly maturing trabecular bone.

FIG. 6 77S sol-gel produced by near-equilibrium drying at 4 weeks post-op. Bone formation is present, but not as extensive as in 58S glass. Arrows indicate resorption of some particles.

FIG. 7 77S sol-gel glass produced by near-equilibrium drying at 8 weeks. Bone formation has proceeded to the center of the defect (red stained regions). About 50% of the particles have resorbed.

FIG. 8 58S sol-gel glass at 8 weeks post-op. Red stained region shows extensive bone formation around and even inside a particle which is clearly resorbing (region labeled at "A"). No inflammatory response is noted.

FIG. 9 77S sol-gel glass at 8 weeks post-op. Bone is noted surrounding particles with no inflammatory response. Resorption of particles can be noted (arrows) although it is slower than in the 58S sol-gel glass.

DETAILED DESCRIPTION OF THE INVENTION

The present invention includes a process for making bioactive glasses in a sol-gel process used for filling osseous defects including a near equilibrium drying step which provides for increased pore size and bioactivity in the final product. The present invention also includes sol-gel bioactive glass compositions. The present invention further relates to materials suitable for bone grafting and repairing of tissue defects where the rate of resorption can be precisely controlled.

As referred to herein, bioactive glasses are typically silicon dioxide based compositions capable of forming HCA when exposed to physiological fluids. Typically, bioactive glasses have the following composition by weight percentage:

$SiO_2$—40–90
CaO—4–45
$Na_2O$—0–10
$P_2O_5$—2–16
$CaF_2$—0–25
$B_2O_3$—0–4
$K_2O$—0–8
MgO—0–5

The process of the present invention includes a drying step which is not included in earlier processes. It has unexpectedly been determined that the use of near-equilibrium drying in place of or in addition to drying under dry conditions used in prior processes provides for much larger average pore size in the final composition at a given level of $SiO_2$ than previously known. It was unexpectedly found that a near equilibrium drying resulted in larger pore size and a higher rate of resorption.

Figure 13:
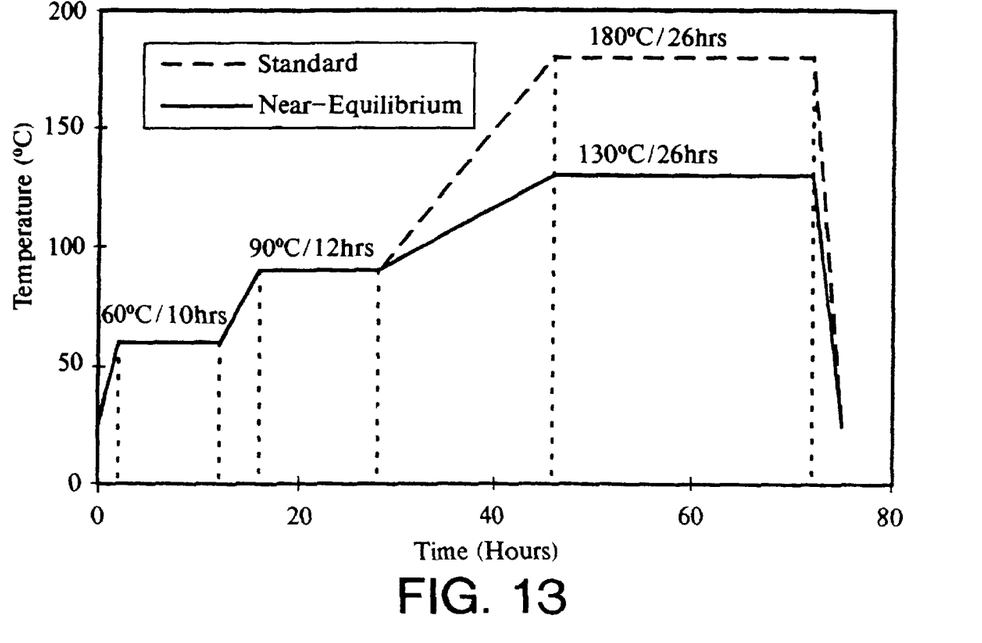
FIG. 13 An example of a drying schedule showing temperature vs. time in standard vs. near equilibrium drying schedules.
Figure 17:
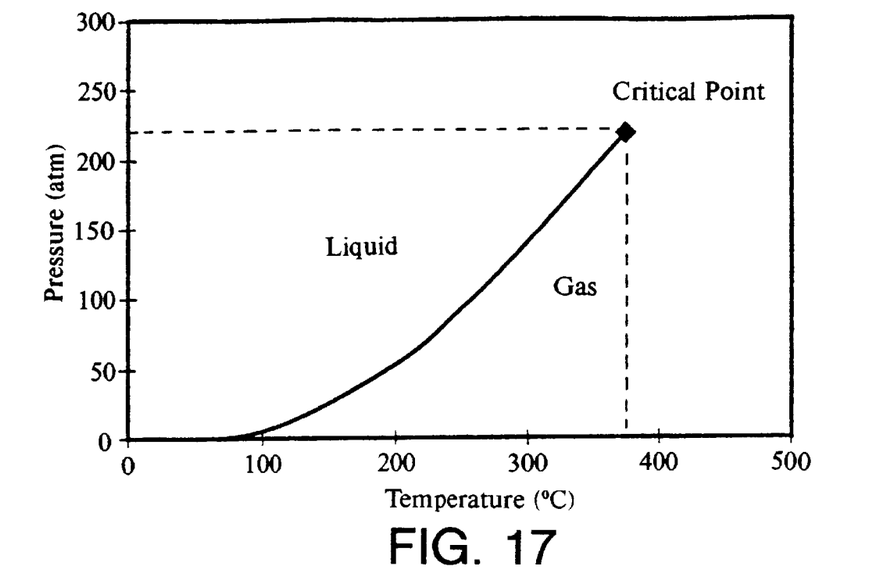
FIG. 17 A phase diagram of water.

Near-equilibrium drying is drying under the conditions near the two phase boundaries in the phase diagram at a temperature and pressure sufficient to yield a bioactive glass with large pore structure i.e. a pore structure sufficient to yield a bioactive glass. For example, near equilibrium drying may be drying under the conditions near the line in the phase diagram of water as shown in FIG. 17 (or other liquids such as methanol, ethanol, acetone, liquid $CO_2$, benzene and so on). By manipulating the sealing of the designed drying chamber to adjust the extent of the drying condition away from the equilibrium line and relative humidity (from environment humidity to 98%), the duration of near-equilibrium drying, and the temperature at which the drying is conducted, one can drastically alter pore size of resultant bioactive glass. For example, increasing the sealing of the drying chamber during drying typically results in an increase in relative humidity and pore diameter. Near-equilibrium drying temperature can also be varied, for example, as depicted in FIG. 13 for the case of water drying. If using other liquids mentioned above than water, one may obtain a faster drying or increase the pore size range of the gel to a large extent.

By manipulating the percentage humidity, the duration of near equilibrium drying, and the temperature at which near equilibrium drying is conducted, one can drastically alter pore size of the resultant bioactive glass. For example, increasing the level of humidity during drying typically results in an increase in pore diameter. Near equilibrium drying temperatures can also be varied, for example, as depicted in FIG. 13. It was unexpected that the change in drying temperature should give rise to such a large change in pore structure and an increase in resorbability.

A sol-gel process in accordance with the present invention is any process that includes the use of a sol-gel in the preparation of bioactive glass. For example, a reaction mixture including tetraethoxysilane (TEOS), triethylphosphate (TEP), and calcium nitrate can be used to make sol-gel bioactive glasses. Alkoxides of calcium, titanium, zirconium, magnesium aluminum, iron and potassium can also be used. Other appropriate ingredients will also be apparent to those of ordinary skill in the art. The present invention also contemplates the use of aerogels. When an aeorogel is used, increased pressure is used instead of near equilibrium drying to achieve larger pore size and greater resorbability.

Sol-gel processing in accordance with the present invention includes a near equilibrium drying step which yields larger pore size in the final product and permits development of HCA very rapidly for both high and low silicon dioxide content gels. Indeed, compositions in accordance with the present invention form HCA more rapidly than prior gels when exposed to SBF (Simulated Body Fluid, Kokubo, T. et al., J. Biomed. Mater. Res., 24, 721–34, 1990) or physiological fluids. The near equilibrium drying technique of the present invention also provides for more homogeneous gels which can be heated to higher temperatures than previous gels while retaining large pore diameter. This permits much better control of the final product e.g. resorbability, homogeneity and physical structure. For example, previous sol-gel compositions were not able to provide adequate resorbability at higher levels of silicon dioxide. Surprisingly, the present invention provides for excellent resorbability even when high amounts of silicon dioxide are included. The sol-gel glasses of the present invention are also more homogeneous than prior sol-gel glasses and calcium is distributed uniformly.

The process of the present invention also provides for bioactive glass capable of resorbing more quickly than known sol-gel bioactive glass materials. For example, in-vivo testing of one embodiment of the present invention showed that more than 50% of sol-gel material made in accordance with the process of the present invention resorbed at eight weeks (see FIGS. 5, 7, 8 and 9). Comparable prior 45S5 melt derived bioactive glasses, as described in the '916 patent which allow bone ingrowth to about the same extent, have not resorbed at all by eight weeks. Indeed, the '916 patent indicates glasses including more than 55% silicon dioxide are not bioactive. Moreover, bioactive glass made by the process of the present invention also exhibits substantially no unwanted inflammatory response.

The drying technique of the present invention can be used to prepare all types of sol-gel bioactive glasses. For example, the process of the present invention can be used to prepare frit, monoliths, powders, coatings, fibers, mats, weaves and composites.

Generally, frit, monoliths, powders, and coatings can be derived from sol-gel processing. Frit can be ground to very broad ranges of particle size such as from about 2 µm up to 1 mm for any purpose. The monolith can be formed to complex shapes such as various implants. Powders can be made to spherical form and from submicron to a few hundred microns. Such compositions are useful, for example, in bone repair and other orthopedic applications, drug delivery, treating tooth hypersensitivity as well as the remineralization of tooth structure, burn healing, and wound healing.

While not being bound to any particular theory, it is believed that the near-equilibrium drying step reduces capillary force inside the pore structure of the gel which results in large pore size. Gels are networks of small colloid particles. The networks includes voids which become pores and pore channels in the final glass composition. It is believed that the moisture of the near-equilibrium drying step enhances the reaction at the neck between two particles in the network and the strength of the neck and "back bone" of the gel structure which reduces shrinkage of the drying structure and ultimately results in gels with large pores.

On the other hand, due to the liquid tension, the pressure difference between the different size of pores and channels is:

$$\Delta P = 2\gamma \cos\theta / r$$

where, $\gamma$ is liquid tension, $\theta$ is contact angle and $r$ is the radius of pores and pore channels. During drying, the pressure difference, $\Delta P$, will pull the network tight enabling pore collapse and gel shrinkage as liquid evaporates. It is believed that near-equilibrium drying allows the liquid inside the pore structure to evaporate under the condition of near-equilibrium at any temperature in FIG. 13. This keeps liquid vapor pressure inside the channels and pores at high heating conditions which resists the shrinkage and collapse of the gel structure and results in large pore sizes.

The following examples are included for purposes of illustration only. They are not intended to narrow the scope of the claims in any way.

Example I—Preparation of Sol-gel Frit

Figure 14:
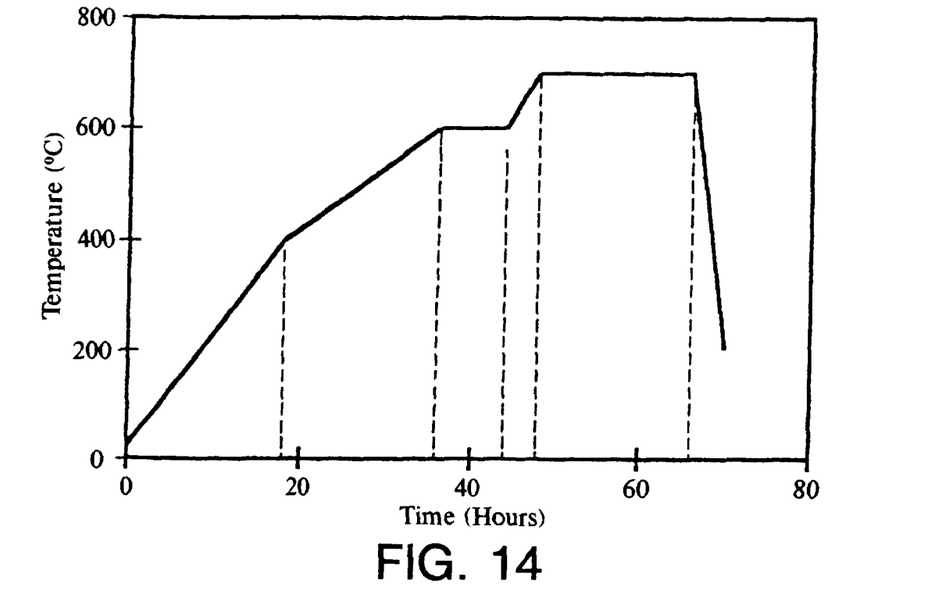
FIG. 14 Example of a heating schedule showing temperature vs. time.

The preparation of sol-gel bioactive glass frit was accomplished as follows:

First, a reaction mixture of deionized water, TEOS, TEP, and calcium nitrate was prepared. Deionized water and hydrochloric acid solutions were combined in a large reactor container. The container was placed on a stirring plate and the solution was stirred using a magnetic stirring bar at medium speed. Then, TEOS was poured into the container and allowed to mix until the solution went clear. The mole ratio of water vs. the mole ratio of TEOS was 4 (other mole ratios can be used e.g. 2–16). After 30 minutes, TEP was added to the stirring solution. In another 20 minutes, calcium nitrate was added. The solution was then stirred for an additional hour then followed by the below steps to make frit:

a. The reaction mixture was transferred to large containers and the containers were placed in an oven for aging at 60° C. for 54 hours;
b. Pore liquor was removed and the aged gels were transferred into a large drying vessel and the vessel was placed inside a designed drying chamber with a proper amount of water. Then, the whole chamber was placed into an oven and dried under the drying schedule in FIG. 13;
c. The dried gels were then heated in a large quartz crucible using the heating schedule of FIG. 14;
d. After drying and heating, the gel cracks and forms large granules. The granules can then be ground to form frit and then separated into various size ranges thus obtained.

The following compositions were prepared by a process including a near equilibrium drying step:

| Sample ID | Si mol % (wt %) | Ca mol % (wt %) | P mol % (wt %) |
|---|---|---|---|
| 77S | 80 (77) | 16 (14) | 4 (9) |
| 68S | 70 (68) | 26 (23) | 4 (9) |
| 58S | 60 (58) | 36 (33) | 4 (9) |

The foregoing compositions were prepared from reaction mixtures prepared as follows:

Sample 77S:

| | | |
|---|---|---|
| 1) D.I. Water: | X × 237 ml | |
| 2) HCl (2N): | X × 44.89 ml | mix 10 minutes |
| 3) TEOS ($Si(OC_2H_5)_4$): | X × 667 ml | mix 30 minutes |
| 4) TEP ($OP(OC_2H_5)_3$): | X × 51 ml | mix 20 minutes |
| 5) $Ca(NO_3)_2 \cdot 4H_2O$: | X × 141.24 g | mix 60 minutes |

Sample 68S

| | | |
|---|---|---|
| 1) D.I. Water: | X × 238.66 ml | |
| 2) HCl (2N): | X × 39.78 ml | mix 10 minutes |
| 3) TEOS ($Si(OC_2H_5)_4$): | X × 663.55 ml | mix 30 minutes |
| 4) TEP ($OP(OC_2H_5)_3$): | X × 58 ml | mix 20 minutes |
| 5) $Ca(NO_3)_2 \cdot 4H_2O$: | X × 260.93 g | mix 60 minutes |

Sample 58S

| | | |
|---|---|---|
| 1) D.I. Water: | X × 377.42 ml | |
| 2) HCl (2N): | X × 62.28 ml | mix 10 minutes |
| 3) TEOS ($Si(OC_2H_5)_4$) | X × 511.19 ml | mix 30 minutes |
| 4) TEP ($OP(OC_2H_5)_3$): | X × 52.10 ml | mix 20 minutes |
| 5) $Ca(NO_3)_2 \cdot 4H_2O$: | X × 324.80 g | mix 60 minutes |

X = Any factor to increase batch size.
× = multiply

Comparison of regular drying with near equilibrium drying schedules:

As can be seen in FIG. 13, the drying temperature is 180° C. for standard drying techniques and, in example, 130° C. for near equilibrium drying of the present invention. The use of lower temperatures in near equilibrium drying maintains higher humidity for a longer period of time (gels can be humidity dried by steam injection into a drying oven). Lower near equilibrium drying temperature also benefits the reaction between necks and strengthens structure.

Near equilibrium drying:

Total drying time was 72 hours as shown in FIG. 13. The proper amount of water was placed in the oven to provide water vapor which maintained humidity around 98% in the first 60 hours at 60° C., 90° C. and 130° C. In the last 12 hours at 130° C., the humidity was decreased gradually from 98% to ambient humidity as water evaporates out.

Comparative Results:

The following results were obtained for near equilibrium dried samples made in accordance with the present invention with heating at 700° C.:

| Sample | % SiO$_2$ | Average Pore Diameter | Surface Area (M$^2$/g) |
|---|---|---|---|
| 58S | 60 | 86 | 207 |
| 68S | 70 | 65 | 305 |
| 77S | 80 | 40 | 389 |

The following results were obtained when the near equilibrium drying step of the present invention is omitted (the process of U.S. Pat. No. 5,074,916) with heating at 700° C.:

| Sample | % SiO$_2$ | Average Pore Diameter | Surface Area (M$^2$/g) |
|---|---|---|---|
| 58S | 60 | 68 | 289 |
| 68S | 70 | 50 | 326 |
| 77S | 80 | 24 (30) | 241 (431) |

( ) = sample heated at 600° C.

As seen above, the near equilibrium drying step of the present invention provides for an unexpected increase in pore size. As further illustrated below, this results in a drastic and unexpected improvement in bioactivity i.e. the ability to form HCA when exposed to in vivo.

In Vivo Bone Implantation

Figure 1:
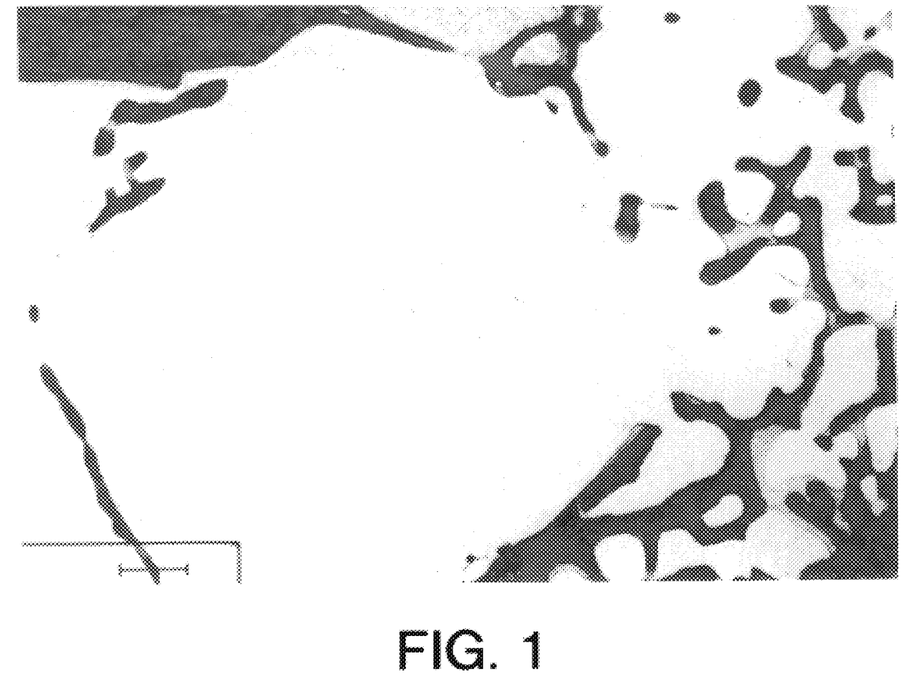
FIG. 1 Surgically created defect 8 weeks post-op. Very little bone formation noted.
Figure 2:
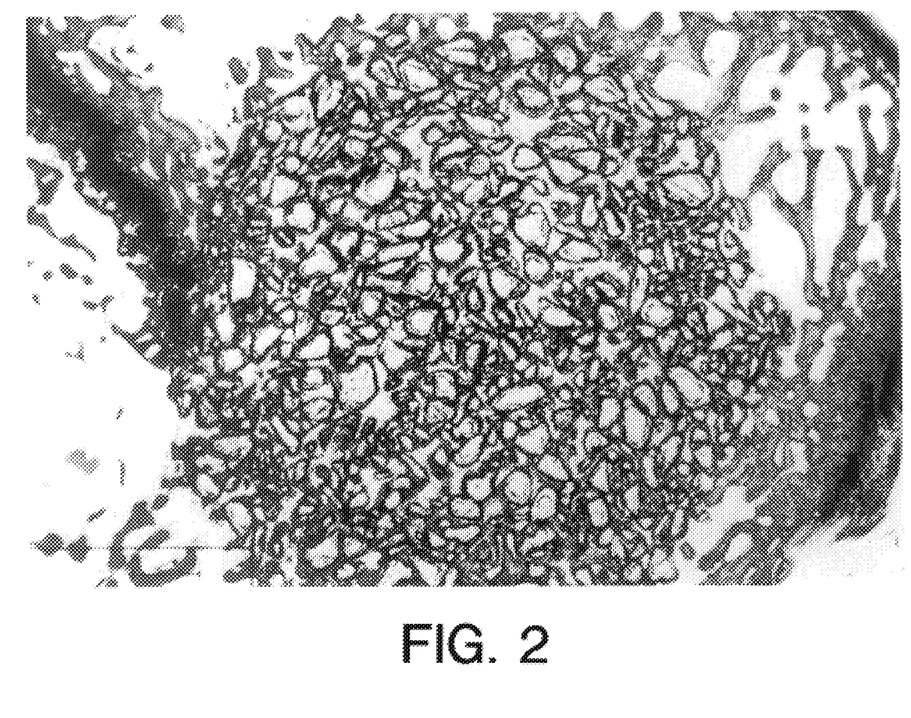
FIG. 2 Melt derived 45S5 Bioglass® at 4 weeks. Red stains show bone formation throughout the defect, especially around particles near the edges of the defect (arrow).
Figure 3:
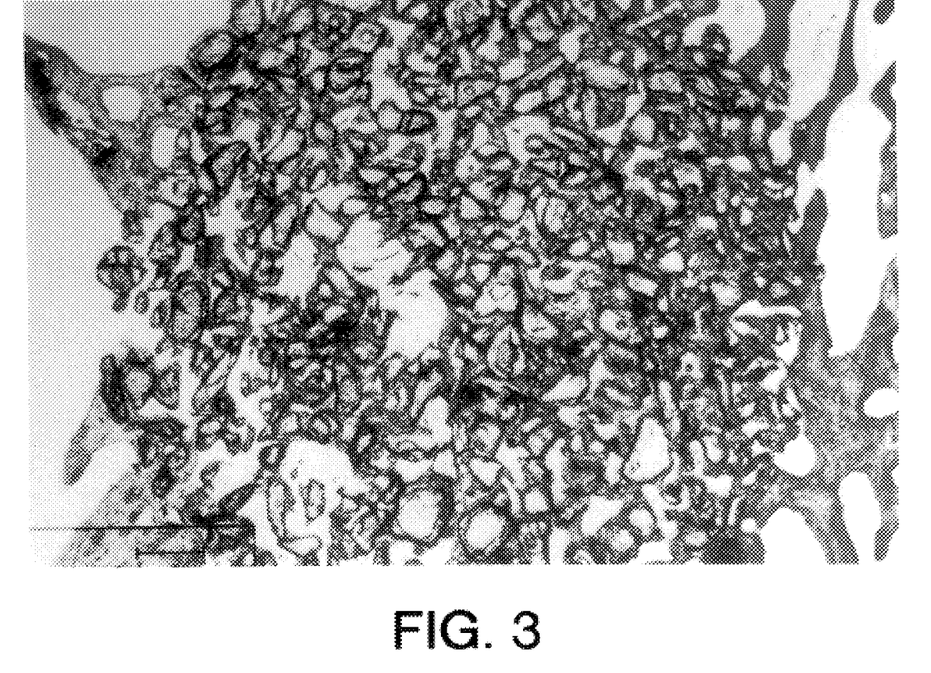
FIG. 3 Melt derived 45S5 Bioglass® at 8 weeks, showing dramatic increase in bond formation, evenly throughout defect. Some resorption of particles is occurring.
Figure 4:
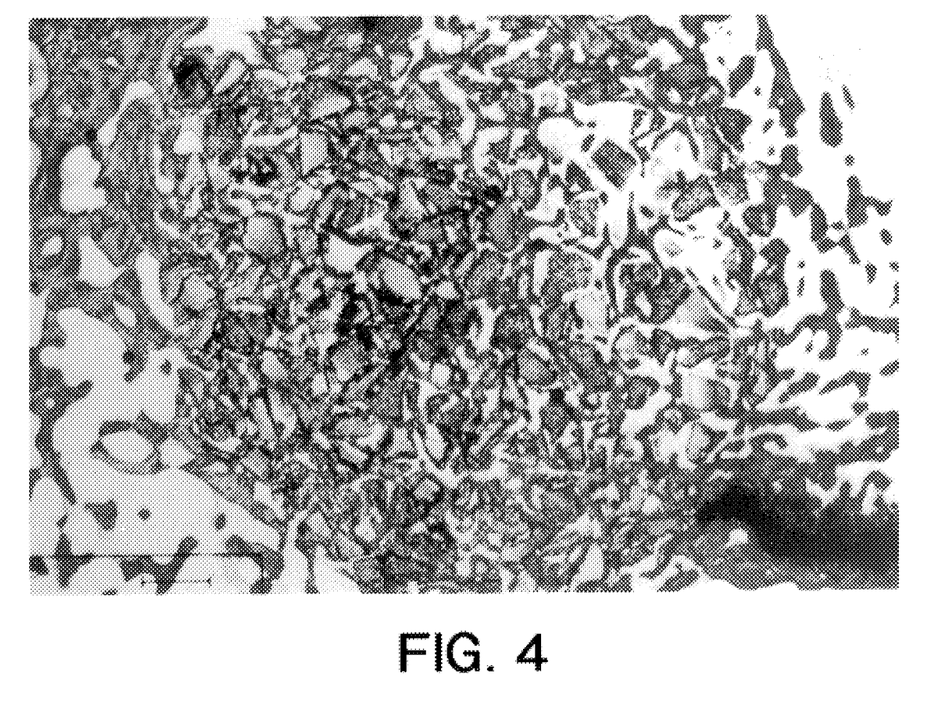
Figure 5:
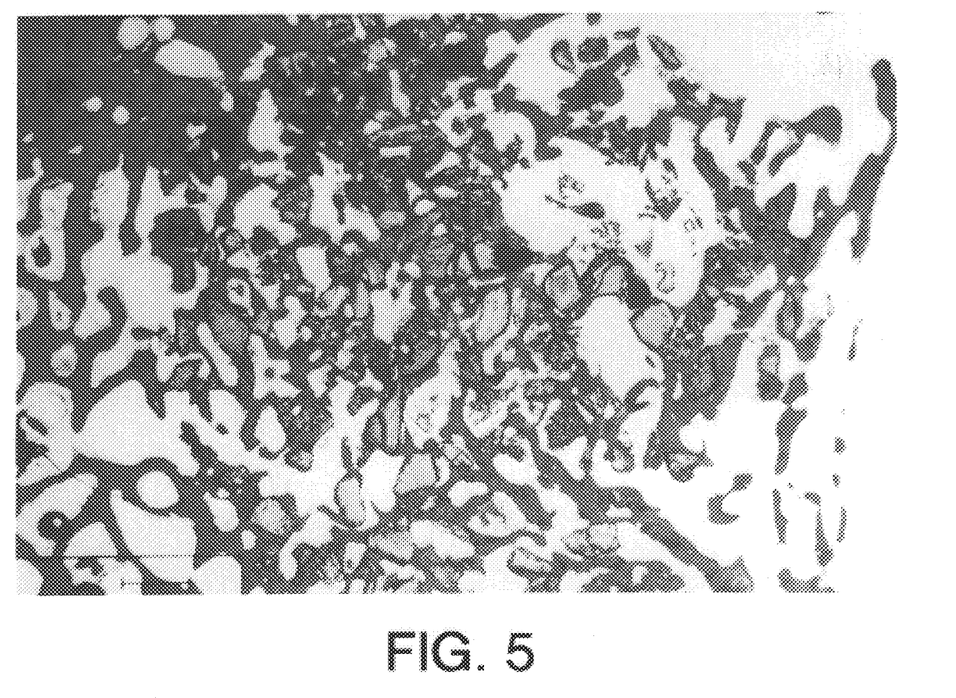
Figure 6:
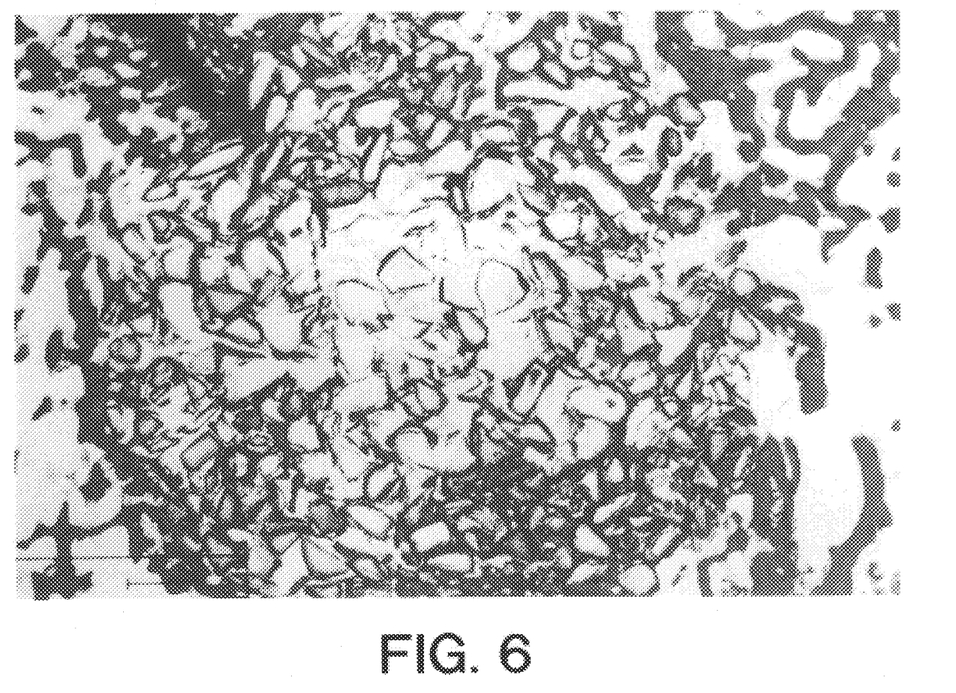
Figure 7:
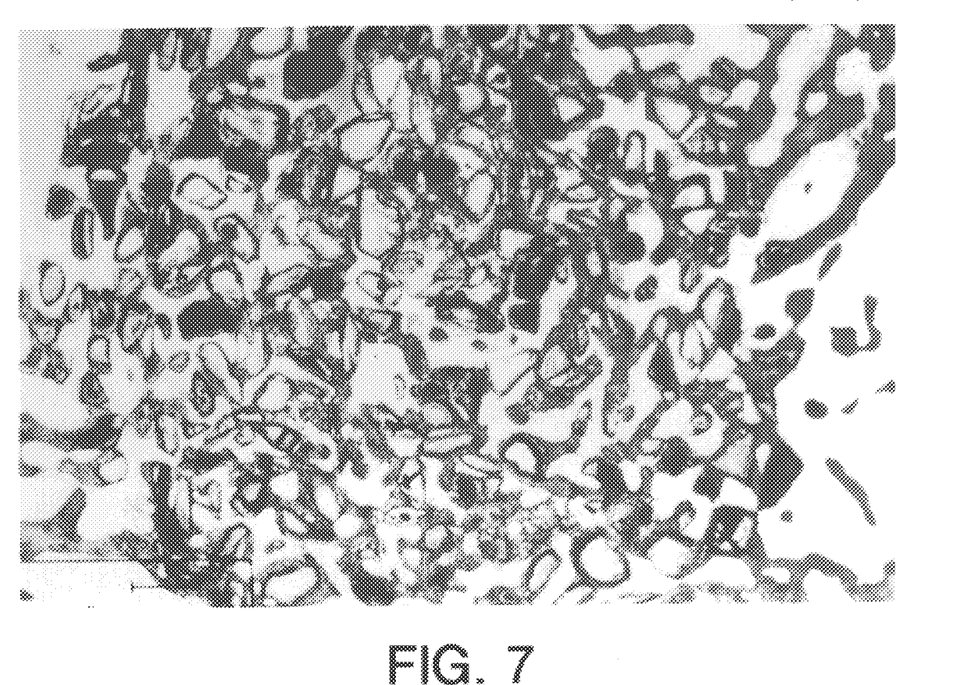
Figure 8:
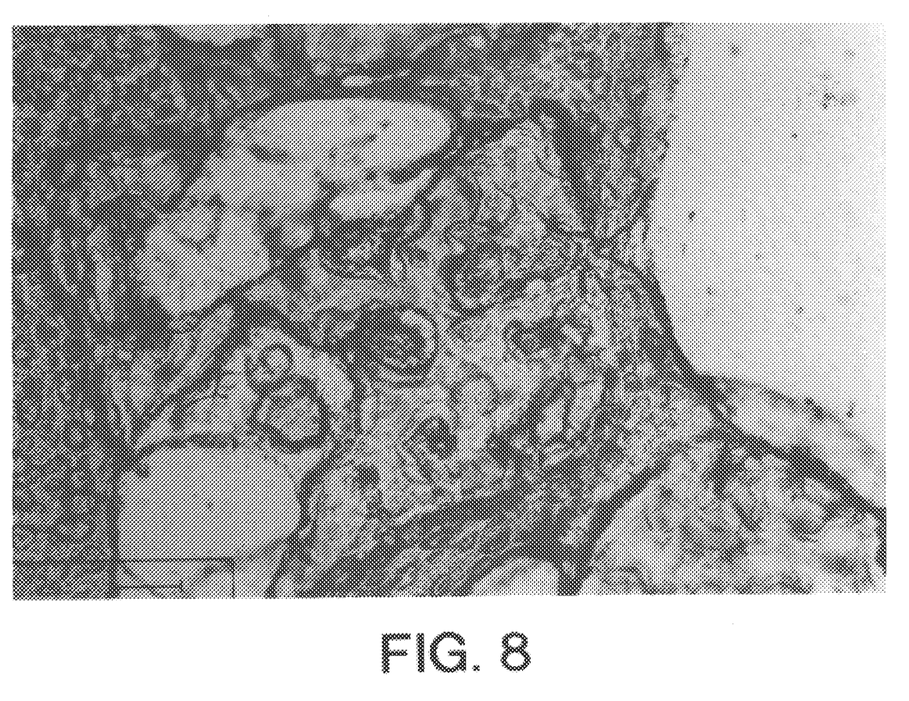
Figure 9:
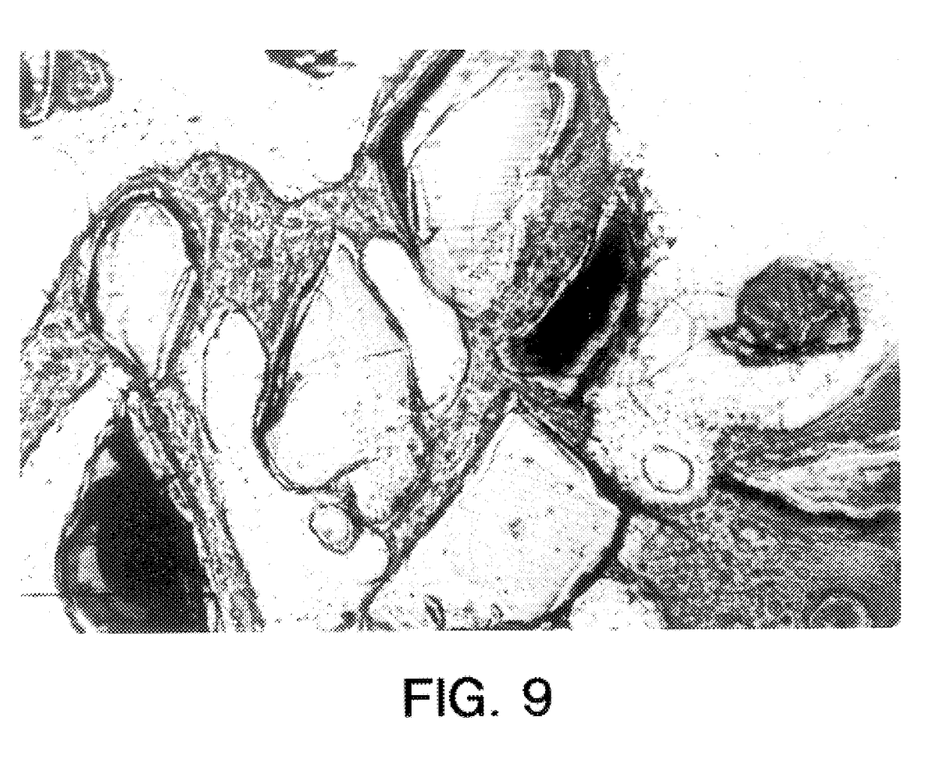

FIGS. 1–9 are photographs indicating the excellent results obtainable by the present invention when compared with other bioactive glasses when exposed in vitro or in vivo. FIG. 1 shows what a surgically created defect looks like 8 weeks post-op. FIGS. 2 and 3 show the results obtained when melt derived bioactive glasses are used. FIGS. 4–9 show the excellent results obtained by the sol-gel of the present invention. FIG. 6 shows resorption in high silica content particles (80% by weight) after only 4 weeks in in vivo. FIG. 7 shows 50% resorption of 80% silica content particles after only 8 weeks in in vivo. Even more dramatic results can be seen in FIGS. 4 and 5 which show extensive resorption in 60% by weight silica bioactive glass compositions after only 4 weeks in in vivo and very advanced resorption after only 8 weeks. This animal model included near equilibrium dried particles in accordance with the present invention of 300–800 microns as measured by optical spectroscopy. The photos of FIGS. 1–9 are rights to histological sections from the animal study.

In Vitro Exposure SBF

Figure 15:
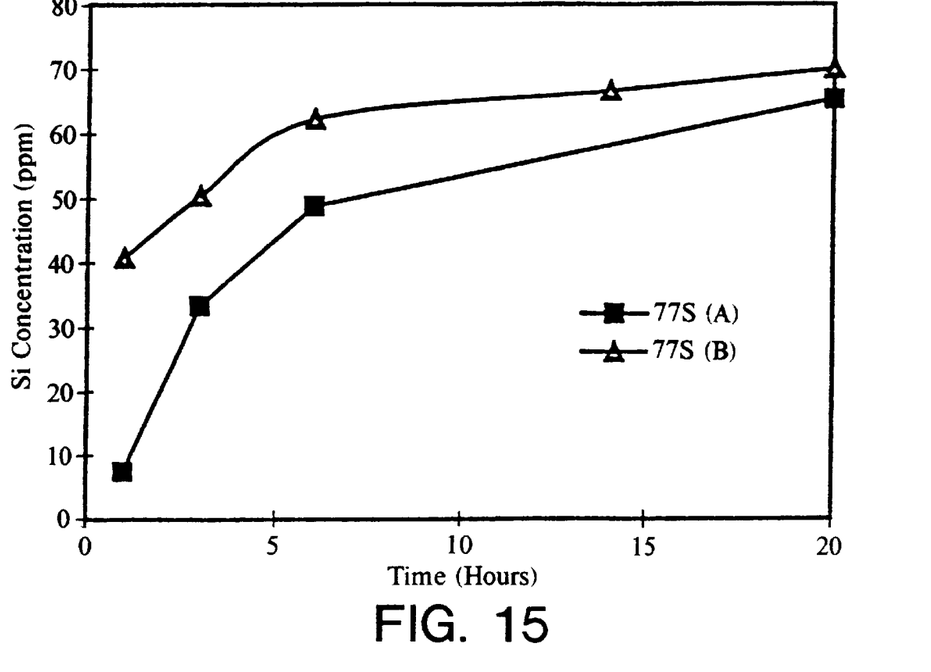
FIG. 15 Silica release of particle prepared in accordance with the present invention vs. a previous sol-gel method disclosed in the '916 patent.
Figure 16:
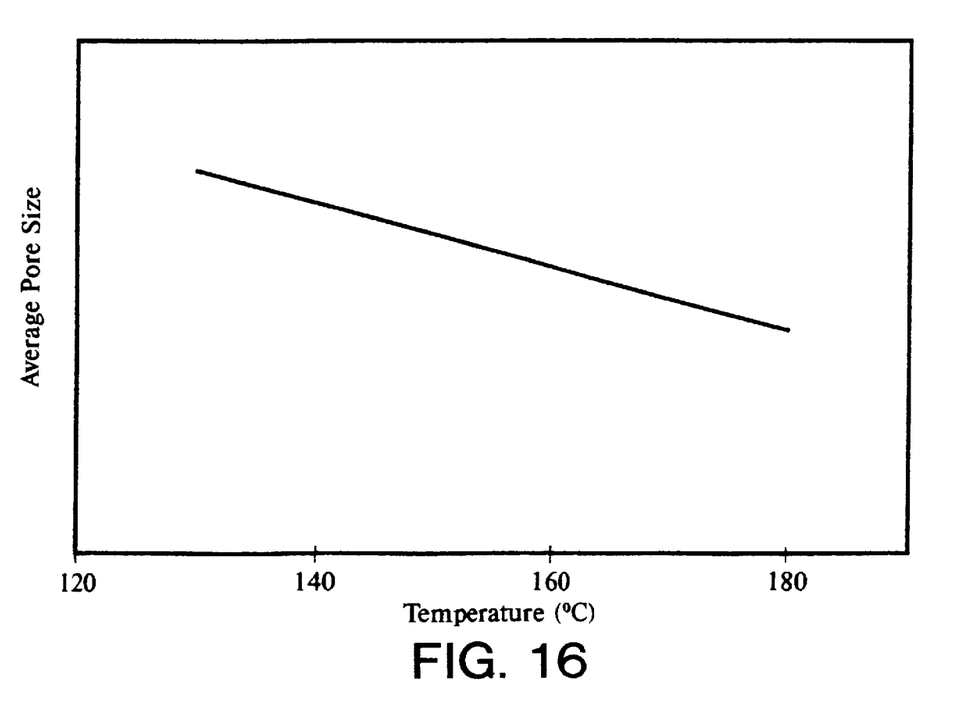
FIG. 16 Diagram of average pore size vs. drying temperature.
Figure 18:
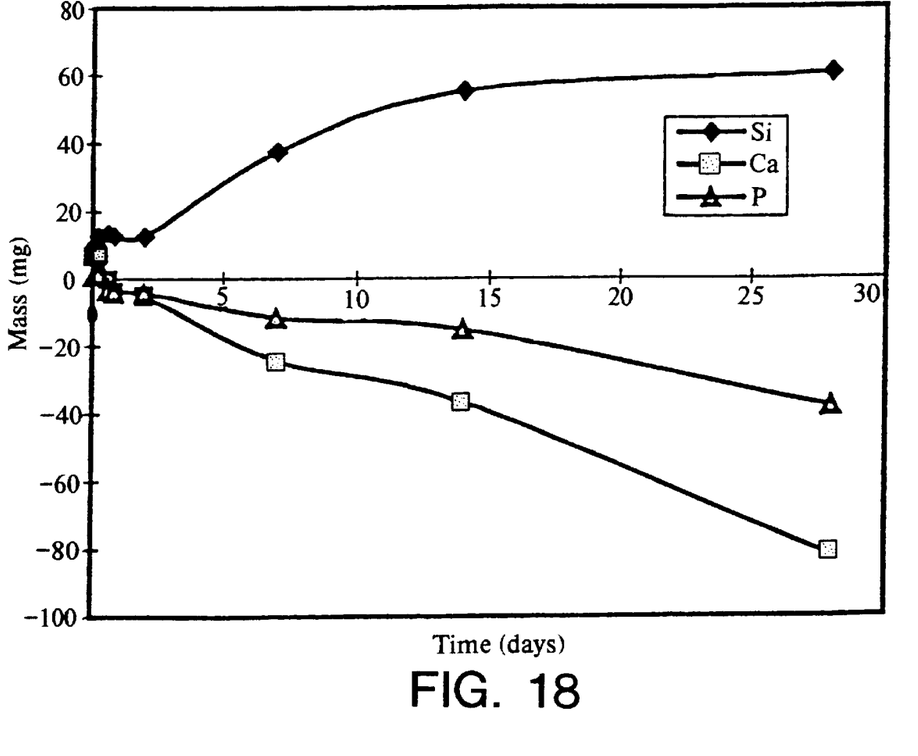
FIG. 18 Ion release of 77(s) in SBF.
Figure 19:
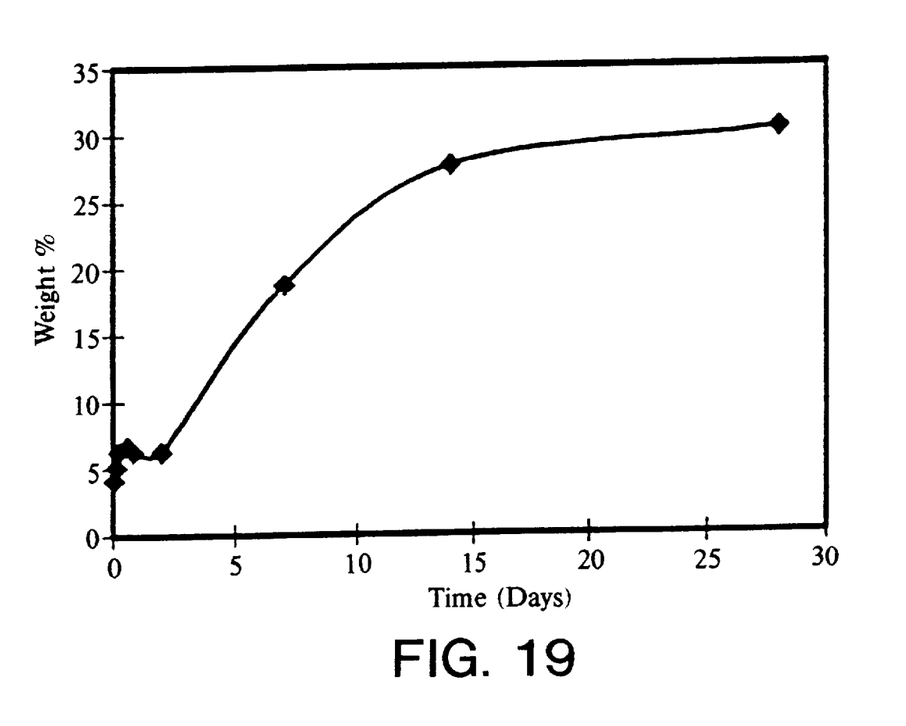
FIG. 19 Si release of 77S(B) in SBF.

Other resorbability testing was also conducted on the foregoing comparative sol-gels. 0.2 g of sol-gel bioactive glass particles of samples 77S(A) [no near equilibrium drying] and 77S(B) [equilibrium dried] were tested in 200 ml of SBF in a centerfuge at 175 RPM over a duration of 1 hr, 6 hrs, 20 hrs, 7 days, 14 days and 28 days. Gel particles with large pore size show greater degradability than small pore size as demonstrated in FIG. 15. 77S(A) had an average pore diameter of 24 angstroms whereas 77S(B) had an average pore diameter of 40 angstroms. As shown in FIG. 18, silica continues to leach from the glasses and calcium and phosphate precipitate back on the particles which simulates the events happening after implantation that induce bone growth while silica dissolves. The negative release of calcium and phosphorous in FIG. 18 implies that calcium and phosphorous precipitate from solution to particles. Thirty percent by weight of silica has been lost in 4 weeks as shown in FIG. 19 which means that these are certainly bioresorbable materials.

FTIR DATA

Figure 10A:
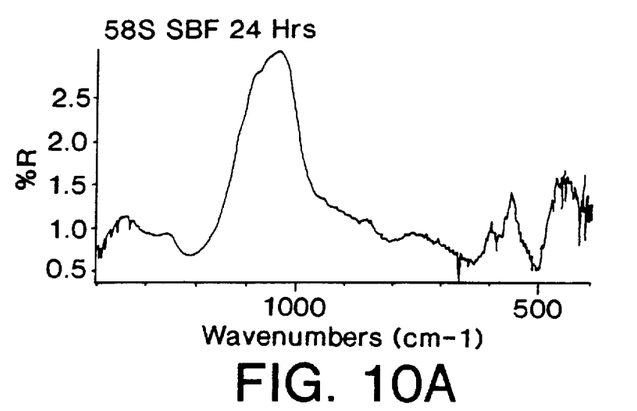
FIG. 10 FTIR spectra of various sol-gel bioactive glass compositions. All have formed extensive HCA layers.
Figure 10B:
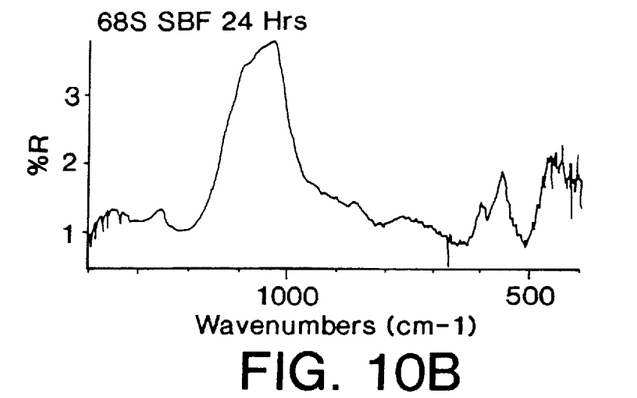
Figure 10C:
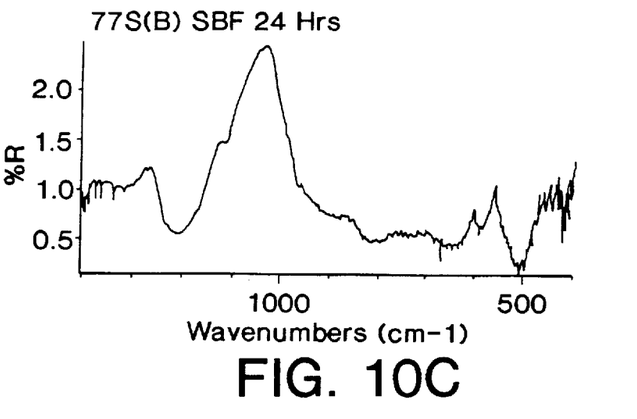
Figure 11A:
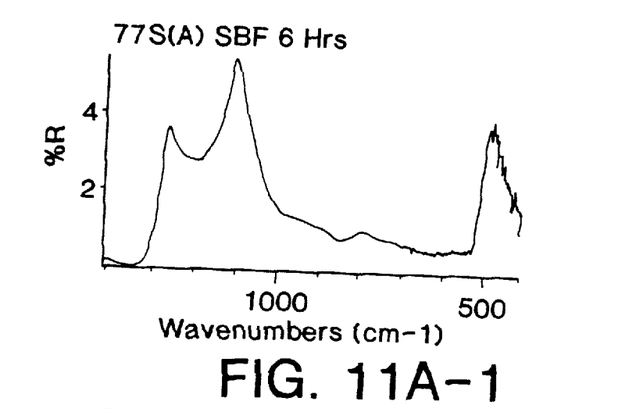
FIG. 11(A) FTIR spectra of sol-gel bioactive glass prepared by previous method A.
FIG. 11(B) FTIR spectra of sol-gel bioactive glass made in accordance with the present invention including a near equilibrium drying step. As seen in the spectra, more rapid formation of HCA is observed when near equilibrium drying is used.
Figure 11A:
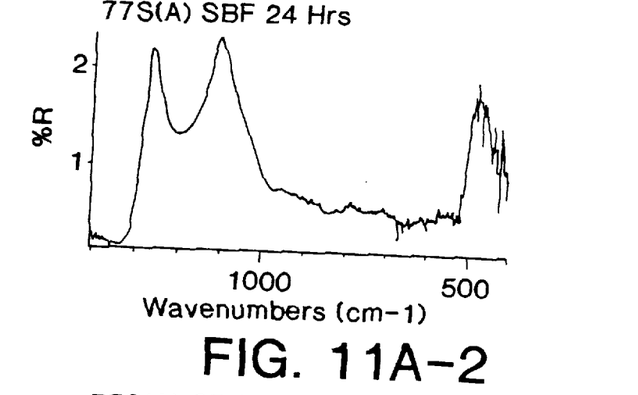
Figure 11A:
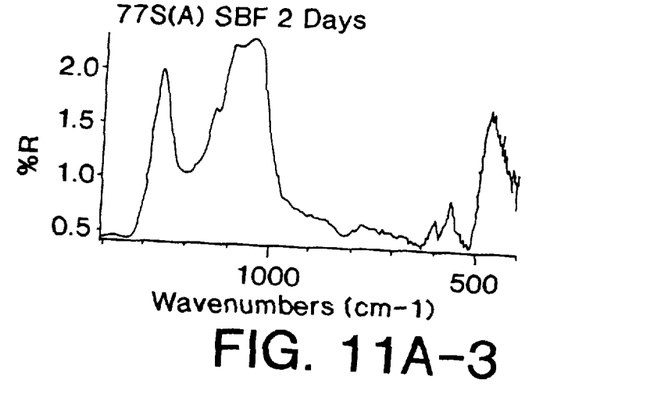
Figure 11B:
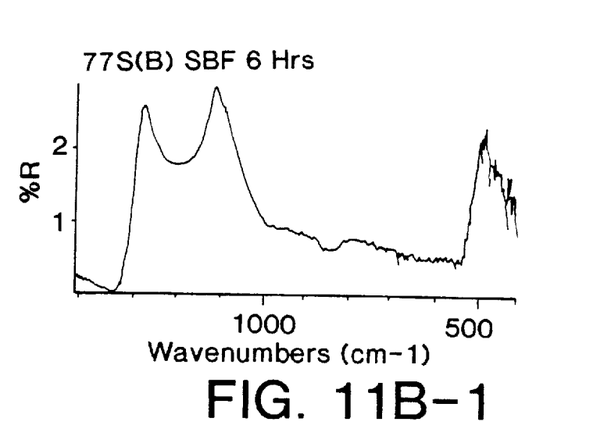
Figure 11B:
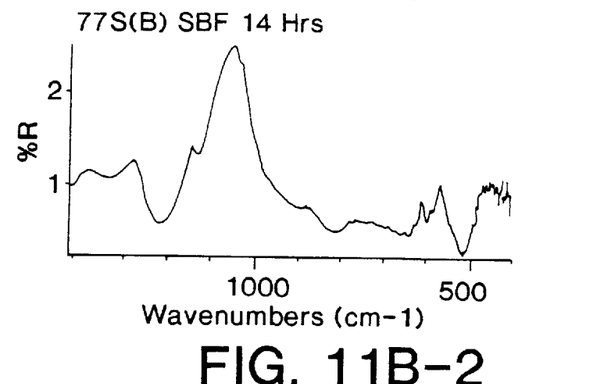
Figure 11B:
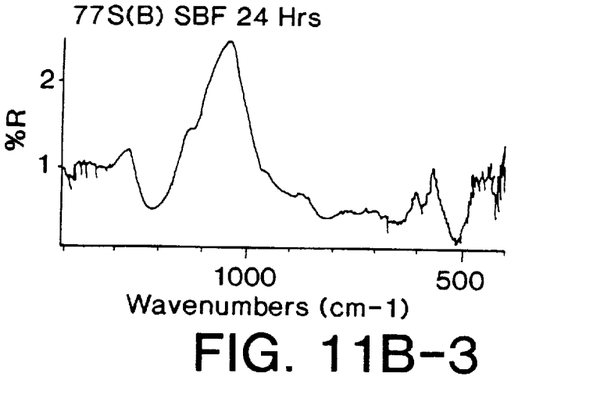

FTIR spectra are used to indicate the formation of HCA on the surface of bioactive glasses that have been exposed to simulated or real body fluids. FIG. 10 shows that samples prepared by a process including near equilibrium drying developed HCA within 24 hours. FIGS. 11(A) and (B) show the FTIR spectra of 77S(A) in accordance with the '916 patent vs. 77S(B) made by a process including near equilibrium drying. It took 2 days to form HCA on the surface of the 77S(A) sample whereas it only took 14 hours to form HCA on the 77S(B) sample which included a near equilibrium drying step.

Example 2—Preparation Of A Monolith

Figure 12A:
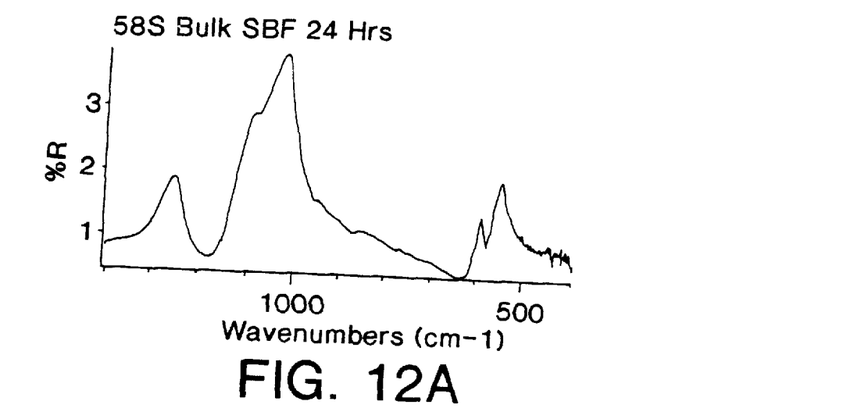
FIG. 12 FTIR spectra of sol-gel bioactive glass monolith after 24 hours in SBF using near equilibrium drying.
Figure 12B:
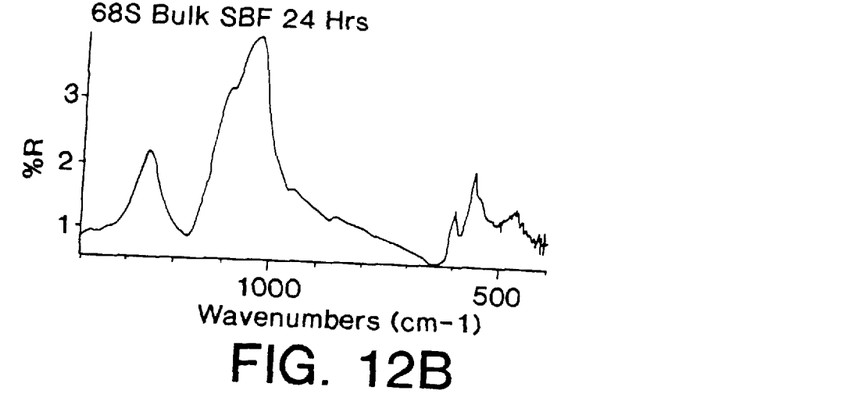
Figure 12C:
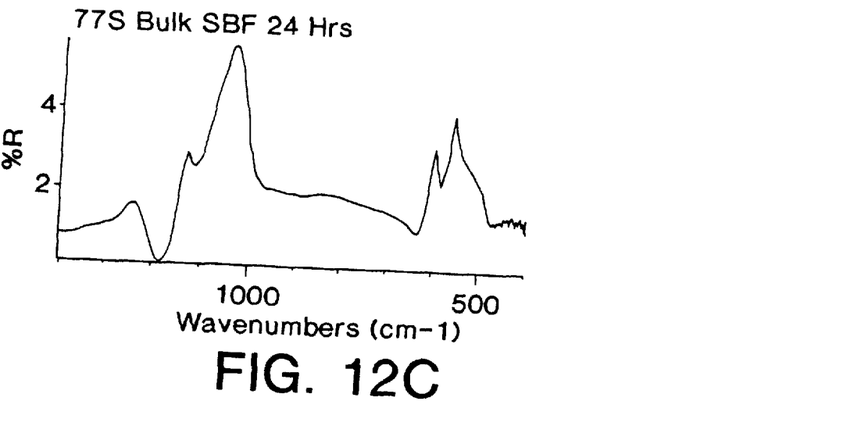

Monoliths must be prepared in a manner that minimizes crack formation. In order to accomplish the manufacture of monoliths of bioactive sol-gel glasses without cracks, others have prepared monoliths by drying under supercritical conditions (C. Jeffrey Brinker, George W. Scherer, "Sol-Gel Science, the Physics and Chemistry of Sol-Gel Processing", Academic Press, 1990) or with chemical additives (L. L. Hench "Science of Ceramic Chemical Processing", pp. 52–64, Wiley 1986). In the present example, an inexpensive method, drying under near equilibrium conditions was used. Water vapor pressure associated with near equilibrium drying yields large pore gels and strengthens the backbone of colloid particle networks to prevent cracking during drying. The resultant bulk monoliths show great bioactivity as seen in FIG. 12. Unlike drying under higher pressure supercritical conditions, near equilibrium drying does not require the use of expensive, complicated equipment. Bioactive aerogels can also be used to prepare monoliths by replacing the near equilibrium drying step with higher pressure. Near equilibrium drying also does not require the use of drying chemicals or high chemical removal temperatures as required by chemical drying additives.

Monoliths were prepared by the following process:

A reaction medium was prepared including deionized water, hydrochloric acid (2N), TEOS, TEP, and calcium nitrate. First, deionized water and hydrochloric acid were combined in a large reaction container and placed on a stirring plate. The solution was stirred using a magnetic stirring bar at medium speed. TEOS was then poured into the container and the solution was allowed to mix until clear. The mole ratio of water to TEOS was 4 (the mole ratio can be varied from, for example, 2–16). After 30 minutes, TEP was added to the stirring solution. In another 20 minutes, calcium nitrate was added. The solution was then stirred for an additional hour then followed by the following steps to make monoliths:

a. The prepared solutions were cast into molds of desired shape and loosely sealed. The molds were then placed in a closed chamber with water for aging for a period of 1–7 days at room temperature;

b. The molds were then sealed tightly and placed in an oven for aging for 54 hours at 60° C.;

c. The pore liquor was then removed from the molds and the shaped gel was quickly transferred into a large drying vessel with a loosely fit cover placed over it. Then, the vessel was placed inside a designed drying chamber with a proper amount of water and the whole chamber was placed into an oven and dried using the drying schedule in FIG. 13;

d. The dried gels were then heated in a quartz crucible using the heating schedule in FIG. 14.

We claim:

1. A process for making bioactive glasses comprising:
   preparing a reaction sol capable of forming a sol-gel;
   aging said reaction mixture;
   near equilibrium drying a gel resulting from the reaction mixture, and;

heating the near equilibrium dried gel at a temperature above ambient.

2. The process of claim 1, further comprising grinding the near equilibrium dried gel.

3. The process of claim 2, further comprising classifying the ground near equilibrium dried gel to various particle size ranges.

4. The process of claim 1, said aging conducted at a temperature of at least about 40° C.

5. The process of claim 1, said aging conducted for a duration of at least about 35 hours.

6. The process of claim 1, said near equilibrium drying conducted at about 60 to 98% humidity.

7. The process of claim 1, said near equilibrium drying conducted at a temperature of between about 130° C. to about 180° C. over at least part of the duration of the near equilibrium drying step.

8. The process of claim 1, said near equilibrium drying conducted at temperatures varied over time between about 130° C. to about 180° C.

9. The process of claim 8, said near equilibrium drying conducted at a temperature ramp with a positive time vs. temperature slope over at least part of the duration of said near equilibrium drying step.

10. The process of claim 1, the heating step conducted at between about 200° C. to about 700° C. over at least part of the duration of the heating step.

11. The process of claim 1, the heating step conducted at temperatures varying over time between 200° C. to about 700° C. over at least part of the duration of the heating step.

12. The process of claim 11, the heating step conducted at a temperature ramp with a positive time vs. temperature slope over at least part of the duration of said heating step.

13. The process of claim 1, the reaction mixture including water, hydrochloric acid, tetraethoxysilane, triethylphosphate, or calcium nitrate, or mixtures thereof.

14. A process for making bioactive glasses by a sol-gel process, the improvement comprising near equilibrium drying a sol-gel.

15. The process of claim 14, wherein said near equilibrium drying is accomplished at about 60 to 98% humidity.

16. The process of claim 14, the improvement further comprising near equilibrium drying at a temperature up to about 150° C.

17. The process of claim 14, the improvement further comprising near equilibrium drying at an initial temperature of less than about 100° C. and a final temperature of less than about 150° C.

18. A sol-gel process for making a bioactive glass monolith comprising:

preparing a reaction mixture capable of forming a bioactive sol-gel monolith;

casting the reaction mixture into a mold of desired shape;

aging said reaction mixture cast in said mold at a temperature elevated above ambient;

near equilibrium drying the reaction mixture, and;

heating the reaction mixture.

19. The process of claim 18, wherein the reaction mixture comprises deionized water, hydrochloric acid, nitric acid, tetraethoxysilane, triethylphosphate or calcium nitrate or mixtures thereof.

20. The process of claim 18, further comprising conducting a pre-aging step before said aging, wherein said pre-aging comprises aging the reaction mixture at ambient temperature.

21. The process of claim 18, further comprising removing a pore liquor after said aging and before said near equilibrium drying.

22. A near equilibrium-dried sol-gel monolith comprising the product of the process of claim 18.

23. A composition for the treatment of orthopedic conditions comprising a bioactive sol gel glass capable of forming an HCA layer within 12 hours of exposure to simulated body fluids.

24. The composition of claim 23, wherein said glass is capable of forming an HCA layer within 5 hours of exposure to simulated body fluids.

25. The composition of claim 23, wherein said glass is capable of forming an HCA layer within 2 hours of exposure to simulated body fluids.

26. The composition of claim 23, wherein said glass is more than 50% resorbed 8 weeks after implantation into a patient.

27. The composition of claim 23, wherein said glass further comprises at least 77% silicon dioxide.

* * * * *